United States Patent [19]

Kojima et al.

[11] Patent Number: 5,268,364

[45] Date of Patent: Dec. 7, 1993

[54] METHOD FOR INHIBITING SELECTIN-DEPENDENT ADHESION OF LEUKOCYTES AND PLATELETS BY O-GLYCOSYLATION MODIFICATION

[75] Inventors: Naoya Kojima; Kazuko Handa, both of Seattle; Sen-Itiroh Hakomori, Mercer Island, all of Wash.

[73] Assignee: The Biomembrane Institute, Seattle, Wash.

[21] Appl. No.: 805,949

[22] Filed: Dec. 12, 1991

[51] Int. Cl.$^5$ .................... A61K 31/70; A01N 43/04
[52] U.S. Cl. ........................... 514/25; 536/4.1; 536/17.2; 536/17.4; 536/17.9; 536/18.7
[58] Field of Search ................ 514/25; 536/4.1, 17.2, 536/17.4, 17.9, 18.7

[56] References Cited

U.S. PATENT DOCUMENTS

| | | | |
|---|---|---|---|
| 4,632,780 | 12/1986 | Seidah et al. | 530/306 |
| 5,049,659 | 9/1991 | Cantor | 530/350 |
| 5,097,023 | 3/1992 | Ducep et al. | 536/17.4 |

*Primary Examiner*—Ronald W. Griffin
*Attorney, Agent, or Firm*—Sughrue, Mion, Zinn, Macpeak & Seas

[57] ABSTRACT

O-glycosylation and O-glycosylation extension inhibitors influence selectin-dependent interactions between cells and between cells and platelets.

15 Claims, 6 Drawing Sheets

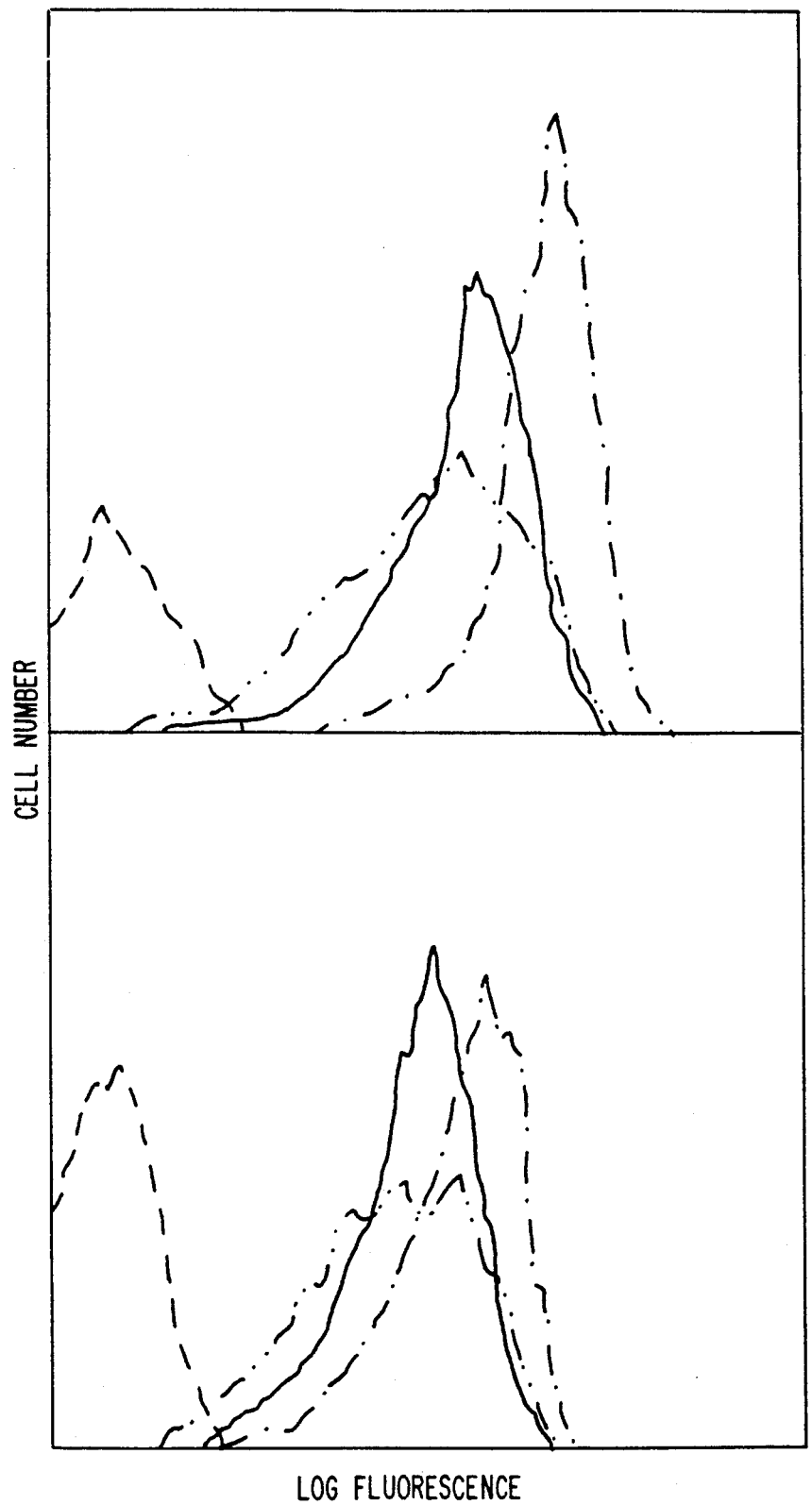

PMA ACTIVATED

THROMBIN ACTIVATED

METHOD FOR INHIBITING SELECTIN-DEPENDENT ADHESION OF LEUKOCYTES AND PLATELETS BY O-GLYCOSYLATION MODIFICATION

BACKGROUND OF THE INVENTION

Selectins are a family of molecules, including ELAM-1 (endothelial leukocyte adhesion molecule-1), GMP-140 (CD62; PADGEM) and LECCAM-1 (Mel-14 in mice, Leu-8 in humans), which primarily mediate adhesion of blood cells and tumor cells expressing specific carbohydrate epitopes to endothelial cells (EC's) and to platelets. The molecules share a structural motif consisting of an N-terminal lectin domain (carbohydrate-binding domain), an epidermal growth factor (EGF) domain, a complement-regulatory sequence repeat, a transmembrane domain and a cytoplasmic C-terminal domain.

The lectin domains of ELAM-1 and GMP-140 bind to the carbohydrate structures sialosyl-Le$^x$ (SLe$^x$) (Lowe et al., Cell, 63: 475, 1990; Phillips et al., Science, 250: 1130, 1990; Polley et al., Proc. Natl. Acad. Sci., U.S.A., 88: 6224, 1991) and sialosyl-Le$^a$ (SLe$^a$) (Berg et al., J. Biol. Chem., 266: 14869, 1991; Takada et al., Biochem. Biophys. Res. Commun., 179: 713, 1991; Handa et al., Biochem, Biophys. Res. Commun., in press). Because SLe$^x$ and SLe$^a$ are tumor-associated antigens (Hakomori, Adv. Cancer Res., 52: 331, 1989), selectins likely play important roles in defining tumor cell adhesion to platelets and EC's and in initiating metastasis (Hakomori, Curr. Opin. Immunol., 3: 646, 1991).

Interaction of leukocytes recruited to an inflammatory locus with activated vasculature endothelial cells, or with activated platelets, is an initial event in inflammation. In general, however, the number of recruited leukocytes is excessive resulting in, for example, infiltration of leukocytes through the vessel walls into surrounding tissue or development of emboli and microemboli resulting from the aggregation of leukocytes with platelets or other blood cell components.

Interaction between tumor cells and activated platelets or activated vasculature endothelial cells can result in events similar to those described above for leukooytes, namely adhesion and development of emboli and mioroemboli. Adhesion of tumor cells to endothelial cells and extravasation or extravascularization of tumor cells are regarded as early events of metastasis.

In the adhesion of either leukocytes or tumor cells to endothelial cells or platelets, interleukin-1 (IL-1) is produced by leukocytes IL-1 induces the expression of ELAM-1. Many tumor cells produce TGF$\beta$ or TNF$\alpha$ which activate endothelial cells and induce expression of ELAM-1. Further, both leukocytes and tumor cells release enzymatic factors and ADP which activate platelets and induce expression of GMP-140.

ELAM-1 and GMP-140 are instrumental in mediating adhesion of tumor cells or leukocytes that express SLe$^a$ or SLe$^x$ to endothelial cells. Similarly, activated platelets expressing GMP-140 adhere tumor cells or leukocytes expressing SLe$^a$ or SLe$^x$.

Accordingly, it would be beneficial to minimize or to prevent adhesion of leukocytes or tumor cells to endothelial cells or to platelets through inhibition of selectin expression, or of SLe$^a$ or SLe$^x$ expression on leukocytes or tumor cells, thereby minimizing or preventing thromboses/embolism, inflammation, tissue damage and metastasis resulting therefrom.

SUMMARY OF THE INVENTION

It is an object of the instant invention to provide a composition and method for minimizing or preventing adhesion of leukocytes or tumor cells to endothelial cells or to platelets wherein that adhesion is mediated by selectins expressed on the endothelial cells or platelets.

That and other objects have been attained in the development of a composition and method for inhibiting the expression of carbohydrate structures expressed on leukocytes or tumor cells that are recognized and bound by the lectin domain of selectin molecules expressed on the surface of endothelial cells and platelets.

The instant invention relates to a composition and method for blocking expression of SLe$^x$ or SLe$^a$ by inhibiting O-glycosylation or extension of O-glycosylation. Systematic studies have shown that an inhibitor of O-glycosylation extension, but not inhibitors of N-glycosylation, block expression of SLe$^x$ or SLe$^a$ by leukocytes or tumor cells and thereby inhibit adhesion of leukocytes or tumor cell to endothelial cells and platelets.

BRIEF DESCRIPTION OF THE DRAWINGS

In FIG. 1A, the—curve represents untreated HL60 cells; the—·—curve represents HL60 cells treated with Bz-$\alpha$-GalNAc and with SNH4; and the—curve represents HL60 cells treated with Bz-$\alpha$-GalNAc and with a control antibody. In FIG. 1B, the curve—represents untreated HL60 cells and the—·—curve depicts HL60 cells exposed to Bz-$\alpha$-GalNAc prior to exposure to the lectin.

FIGS. 2A and 2B depict flow cytometric traces of HL60 cells exposed to N-glycosylation inhibitors, castanospermine and swainsonine. The —curve depicts untreated HL60 cells; the ——depicts HL60 cells treated with castanospermine and with an SLe$^x$ antibody, SNH3 in FIG. 2A and SNH4 in FIG. 2B; the—·—curve depicts HL60 cells treated with swainsonine; and the—·—curve depicts HL60 cells treated with castanospermine and with a control non-specific mouse IgG or IgM antibody.

In FIG. 3A the solid bars represent unactivated endothelial cells and open bars represent activated endothelial cells. Myelogenous HL60 cells, colonic Colo205 tumor cells and monocytic U937 leukemia cells either were unexposed (−) or exposed (+) to Bz-$\alpha$-GalNAc.

DETAILED DESCRIPTION OF THE INVENTION

Figures 1A, 1B:
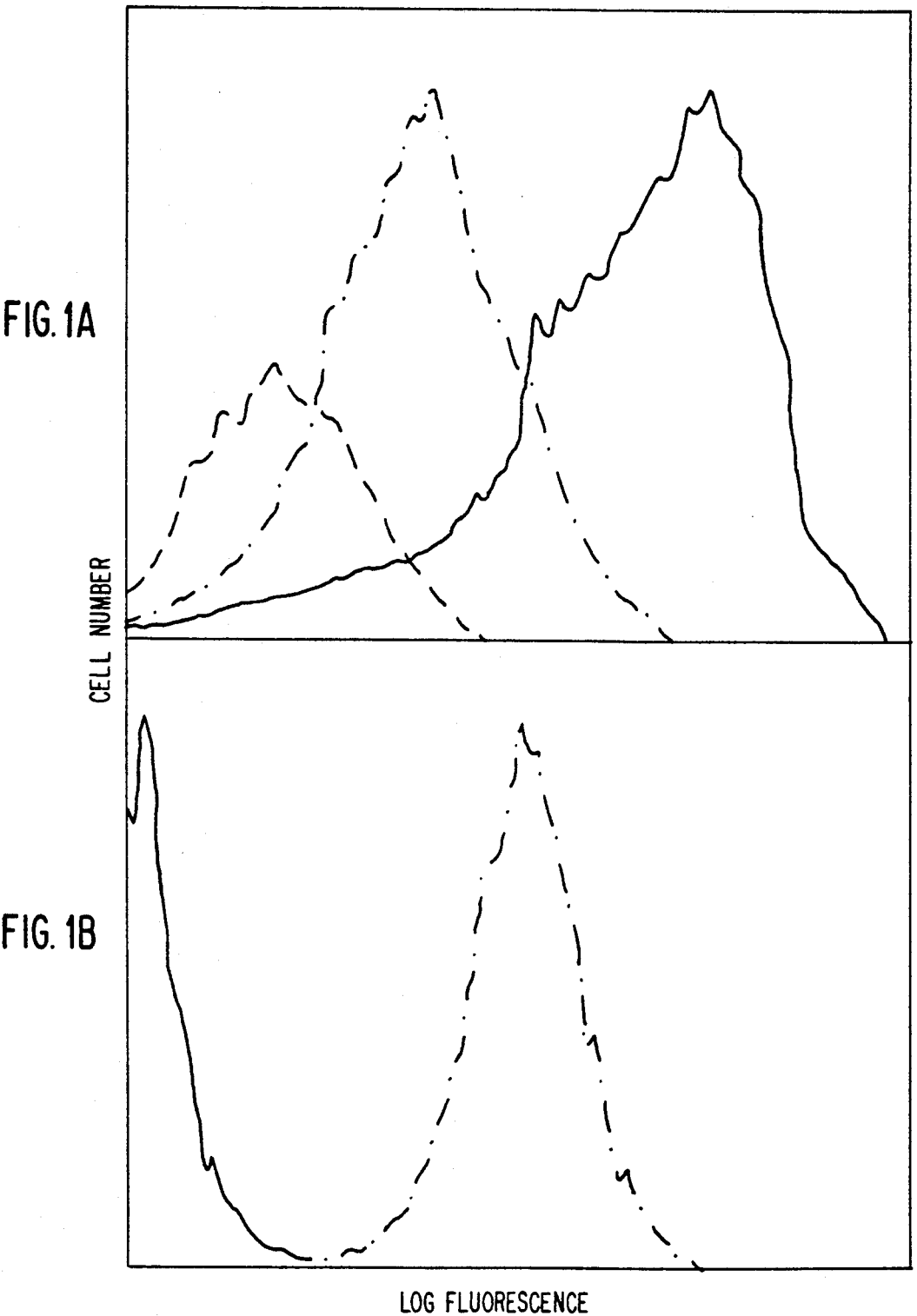
FIGS. 1A and 1B depict graphs of fluorescent cells detected in a flow cytometer. HL60 cells, either untreated or treated with Bz-$\alpha$-GalNAc, were then exposed to an antibody which binds specifically to SLe$^x$ (SNH4), FIG. 1A (or to fluorescence labelled Helix pomatia lectin which binds to the structure, O-$\alpha$-GalNAc, FIG. 1B) and to the appropriate fluorescence labelled secondary antibody. The graphs depict the number of cells and various levels of fluorescence intensity.

As used herein, "cell" includes nucleated and enucleated elements, such as platelets.

"Leukocytes" are cells normally associated with the blood and lymph systems including neutrophils, macrophages and lymphocytes or any other cell that expresses a ligand that is recognized and bound by a selectin.

The invention relates to a composition and method for inhibiting adhesion of leukocytes and tumor cells to endothelial cells and platelets through the binding function of selectins (selectin-dependent adhesion). That is obtained by exposure of cells to inhibitors of O-glycosylation or O-glycosylation extension.

Glycosylation in glycoproteins is based on, (i) O-glycosylation of serine (Ser) or threonine (Thr); or (ii) N-glycosylation of asparagine (Asn). Following the binding of a sugar to the amino acid residue, a carbohydrate chain can be developed by the successive addition of further sugar residues to the first conjugated sugar. Thus, the development of a glycoprotein involves the initial glycosylation and can include extension from the monosaccharide derivative to form a polysaccharide chain attached to the amino acid.

Reagents known to modify N-glycosylation or O-glycosylation are known (for example, inhibitors of N-glycosylation are reviewed in Elbein, Ann. Rev. Bio chem., 5 6: 497, 19 87). Dimethyl-nojirimycin, tunicamycin, swainsonine and castanospermine (obtained from Sigma Chemical Co., St. Louis, MO) are suitable inhibitors of N-glycosylation.

Benzyl-α-N-acetylgalactosamine (Bz-α-GalNAc) (also obtained from Sigma) inhibits extension of O-glycosylation leading to accumulation of O-α-GalNAc, the epitope recognized by Helix pomatia lectin (Kuan, J. Biol. Chem., 264: 19271, 1989).

The identification of other O-glycosylation and O-glycosylation extension inhibitors can be obtained using methods known in the art for determining whether O-glycosylation of Ser or Thr has occurred and the size of the sugar chain and identity of the sugar residues contained therein. Whether a specific inhibitor can be used in the practice of the instant invention can be determined by practicing the methods disclosed herein or any other equivalent method for determining whether selectin-dependent adhesion is inhibited thereby.

The carbohydrate epitopes SLe$^x$ and SLe$^a$ of HL60 (myelogenous cells), Colo205 (colon cancer cells) and U937 (monocytic leukemia cells) capable of recognition by selectins are present mainly in the form Of O-linked chains. SLe$^x$ or SLe$^a$ present in N-linked chains may not be recognized efficiently by selectins, particularly by ELAM-1. Although the exact rationale for discriminatory recognition of the same epitope present in O-linked chains, N-linked chains or glycosphingolipids remains unclear, O-linked structures tend to be clustered, as often observed in mucin-type glycoproteins or leukosialin molecules (Fukuda, Glycobiology, 1: 347, 1991). In contrast, N-linked structures do not form clusters.

Bz-α-GalNAc, which inhibits extension of O-linked carbohydrate chains, is an O-glycosylation modifier. However, other O-glycosylation inhibitors could be equally or even more effective in blocking selectin-dependent adhesion of myelogenous cells or tumor cellsiin the practice of the instant invention. Because systemic administration of α-GalNAc is known to be hepatotoxic (Liehr et al., Virchows Arch. B Cell. Path., 26: 331, 1978), microcapsules, such as liposomes, containing high concentrations of Bz-α-GalNAc can be conjugated with anti-Le$^x$ or anti-SLe$^x$ mAb's, thereby enabling the targeting of cells in question and minimizing side effects as a means to block selectin-dependent adhesion of Le$^x$ or SLe$^x$-expressing myelogenous or tumor cells. Alternatively, Le$^x$-expressing liposomes including Bz-α-GalNAc can be used. An interaction between Le$^x$ molecules is known (Eggens et al., J. Biol. Chem., 264: 9476, 1989) and application of such liposomes could effectively target myelogenous cells or tumor cells which express Le$^x$ as well as SLe$^x$.

The O-glycosylation or O-glycosylation extension inhibitor can be administered by any of a variety of art-recognized means. The means, route and treatment regimen are determinable following routine procedures known in the pharmaceutic arts. For example, the O-glycosylation or O-glycosylation extension inhibitor, or pharmaceutically acceptable salt thereof, can be combined with pharmaceutically acceptable diluents, carriers or excipients to provide a medicament. The medicament can take a variety of forms including powder, tablet, gel or solution. Pharmaceutically acceptable diluents include known buffers and salines. The O-glycosylation or O-glycosylation extension inhibitor formulations can be administered by known routes, namely orally, intramuscularly, intravenously and the like.

As mentioned above, the instant invention can be practiced using microcapsules. The making and using of microcapsules, such as liposomes, are known in the art. The use of microcapsules can ensure a locally higher concentration of the active ingredient without the untoward side effects associated with a more systemic route of administration.

The pharmaceutically effective dose regimen can vary as to the disease, age and weight of the patient, for example. An appropriate dosage is determinable using appropriate in vitro test systems, animal models and clinical trials. A suitable dosage is one that is equivalent to approximately 2 mM of Bz-α-GalNAc in vitro Other reagents with greater inhibitory activities of 0-glycosylation or 0-glycosylation extension may be administered at appropriately lowered dosages.

Various aspects of the invention now will be exemplified in the following non-limiting example. Unless noted otherwise, all weights and volumes are as w/v or v/v.

EXAMPLE

HL60 (CCL 200), Colo205 (CCL 222) and U937 (CRL 1593) were obtained from the ATCC. HUVEC's (human umbilical vein endothelial cells) were obtained from Cell Systems (Kirkland, WA). The cells were cultured as recommended by the ATCC or according to known procedures. HUVEC's, cultured essentially according to the methods of Bevilacqua et al. (Proc. Natl. Acd. Sci., 84: 9238, 1987) and Wellicome et al. (J.

Imm., 144: 2558, 1990) were used as confluent monolayers. For activation, the monolayers were exposed to IL-1.

The HL60, Colo205 and U937 cells were exposed to the various inhibitors during culture. Three days prior to assay, the various inhibitor reagents at the noted concentrations were added to the cell cultures. Then the suspensions were centrifuged, the cell pellets obtained therefrom were suspended in fresh medium and then used for the assay.

To confirm that Bz-α-GalNAc inhibited O-glycosylation, HL60 cells were exposed to 2 mM Bz-α-GalNAc for 72 hours and then to antibodies specific for SLe$^x$, SNH3 and SNH4 (Muroi et al., Blood, in press) and for SLe$^a$, CA19-9 (Magnani et al., J. Bio. Chem., 257: 14365, 1982). The primary antibodies were used at a concentration of 2-5 μg/ml per 2×10$^5$ cells. As a control antibody in the experiments, a mouse IgG or IgM obtained from Sigma was used. The secondary antibody was an appropriately titrated FITC-labelled goat anti-mouse Ig antibody obtained from Tago Co. (Burlingame, CA). Number of labelled cells and the degree of fluorescence thereof were assessed in an Epics Profile flow cytometer (Coulter, Hialeah, FL).

Culturing of the cells for 72 hours in the presence of 2 mM Bz-α-GalNAc resulted in complete or nearly complete blocking of expression of SLe$^x$ as measured by reactivity with anti-SLe$^x$ mAb's SNH3 and SNH4. Slight residual reactivity with SNH3 was observed for HL60 cells. For Colo205 and U937 cells cultured with Bz-α-GalNAc, there was no reactivity with SNH3 or SNH4, nor with anti-SLe$^a$ mAb CA19-9. The flow cytometric pattern for HL60 cells reflecting the effect of Bz-α-GalNAc is shown in FIG. 1A. Only Bz-α-GalNAc-treated cells showed greatly reduced reactivity with SNH4 (FIG. 1A).

Treated and untreated HL60 cells also were exposed to appropriately titrated FITC labelled H. pomatia lectin (Sigma) and analyzed in the flow cytometer. Exposure of HL60 cells to Bz-α-GalNAc resulted in significant reactivity with H. pomatia lectin, which recognizes α-GalNAc. Bz-α-GalNAc blocks chain elongation of O-linked carbohydrates at the cell surface resulting in the accumulation of O-linked α-GalNAc without chain elongation (FIG. 1B).

In contrast to the effect of O-glycosylation modification, reagents affecting N-glycosylation, such as 10 μg/ml swainsonine and 100 μg/ml castanospermine (which block formation of N-linked complex-type structures) had no inhibitory effect on SLe$^x$ expression (see FIGS. 2A and 2B for effect of those reagents on HL60 cells). Whereas swainsonine had a negligible effect on SLe$^x$ expression in those cells, castanospermine slightly enhanced SLe$^x$ expression (FIG. 2A, reaction with SNH3; FIG. 2B, reaction with SNH4). Swainsonine slightly reduced adhesion of HL60 cells to activated HUVEC's (see FIG. 4).

Figure 3B:
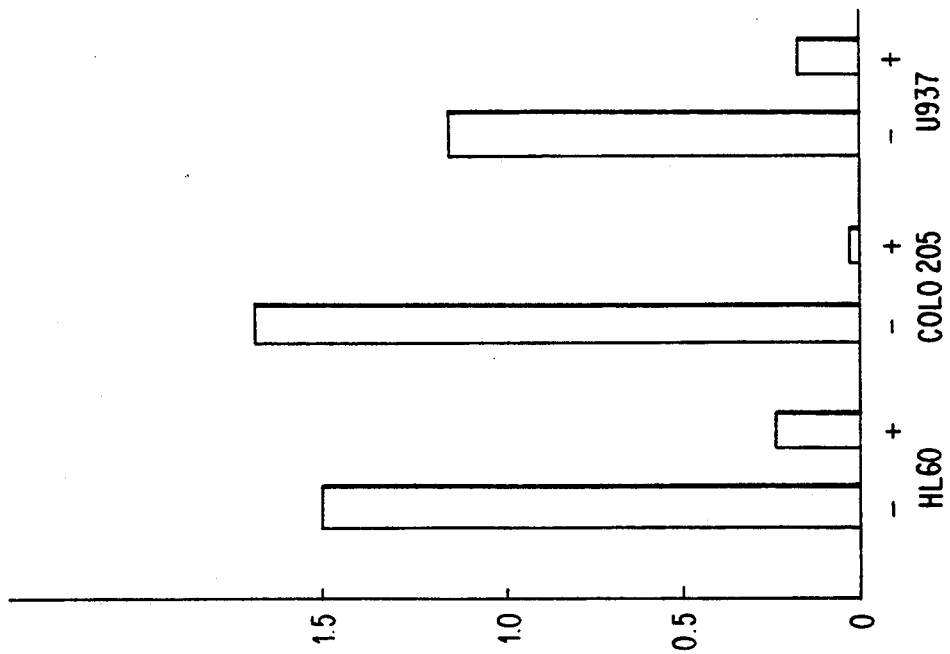
FIGS. 3A and 3B are graphs depicting the binding of treated and untreated HL60, Colo205 and U937 cells to endothelial cells (FIG. 3A) and to an ELAM-1-coated plate (FIG. 3B).

To assess the binding capacity of treated cells to endothelial cells, HUVEC's cultured to confluency were stimulated with 1 U/ml interleukin-1β (IL-1) for 4 hours. Then HL60, Colo205, or U937 cells with or without O-glycosylation inhibition by Bz-α-GalNAc, metabolically labelled with [$^3$H]thymidine according to known procedures, were added to the monolayers. After 1 hour incubation, adherent cells were quantified by conversion of radioactivity count to cell number (FIGS. 3A and 3B).

Figure 3A:
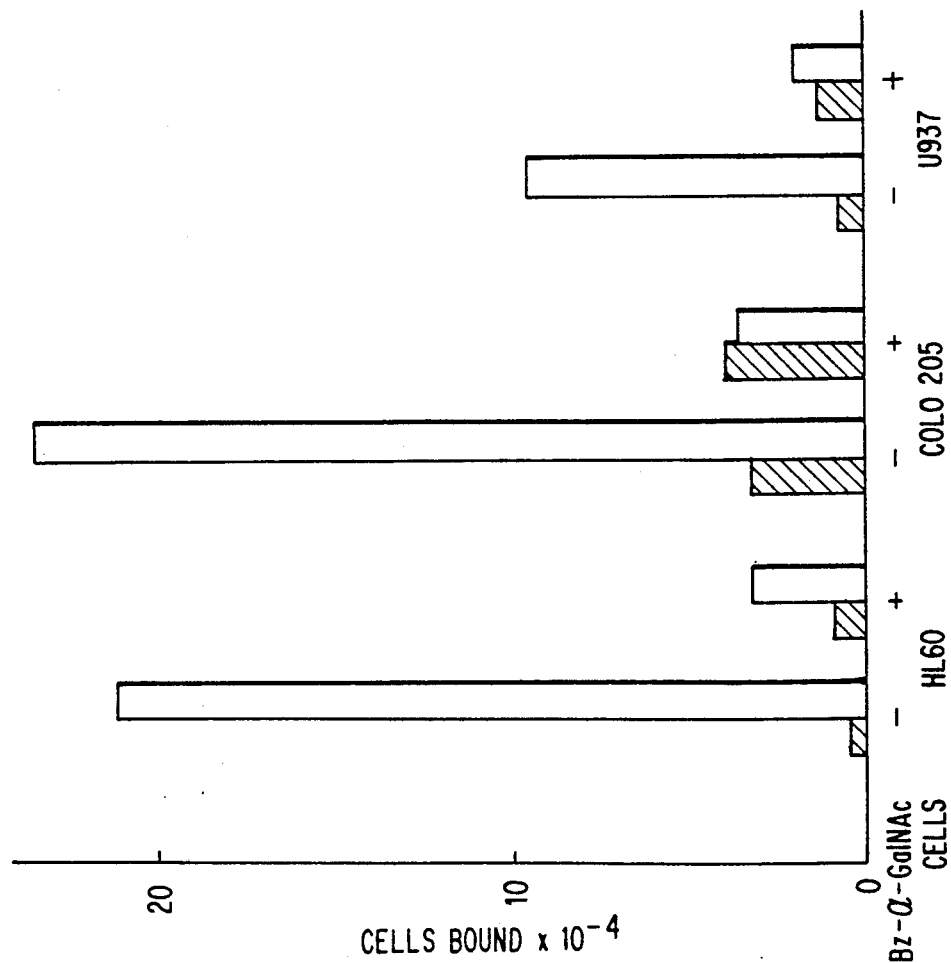

Only those cells treated with 2 mM Bz-α-GalNAc showed clear inhibition of adhesion to stimulated HUVEC's (FIG. 3A). The effect clearly is due to a loss of ELAM-1-dependent adhesion since only Bz-α-GalNAc-treated cells showed significantly reduced adhesion on ELAM-1-coated plastic plates (FIG. 3B). The inhibitory effect of Bz-α-GalNAc was clear for HL60 and Colo205 cells but somewhat less so for U937 cells (FIG. 3A). (The ELAM-1 protein, obtained from Dr. Walter Newman, Otsuka America, Rockville, MD, was applied in 50 μl aliquots of a 0.5 μg/ml in PBS to the wells of a Falcon Probind plate. The plates were incubated overnight at 4° C., the wells were washed with PBS and then blocked with a 1% BSA solution prior to use.)

Figure 4A:
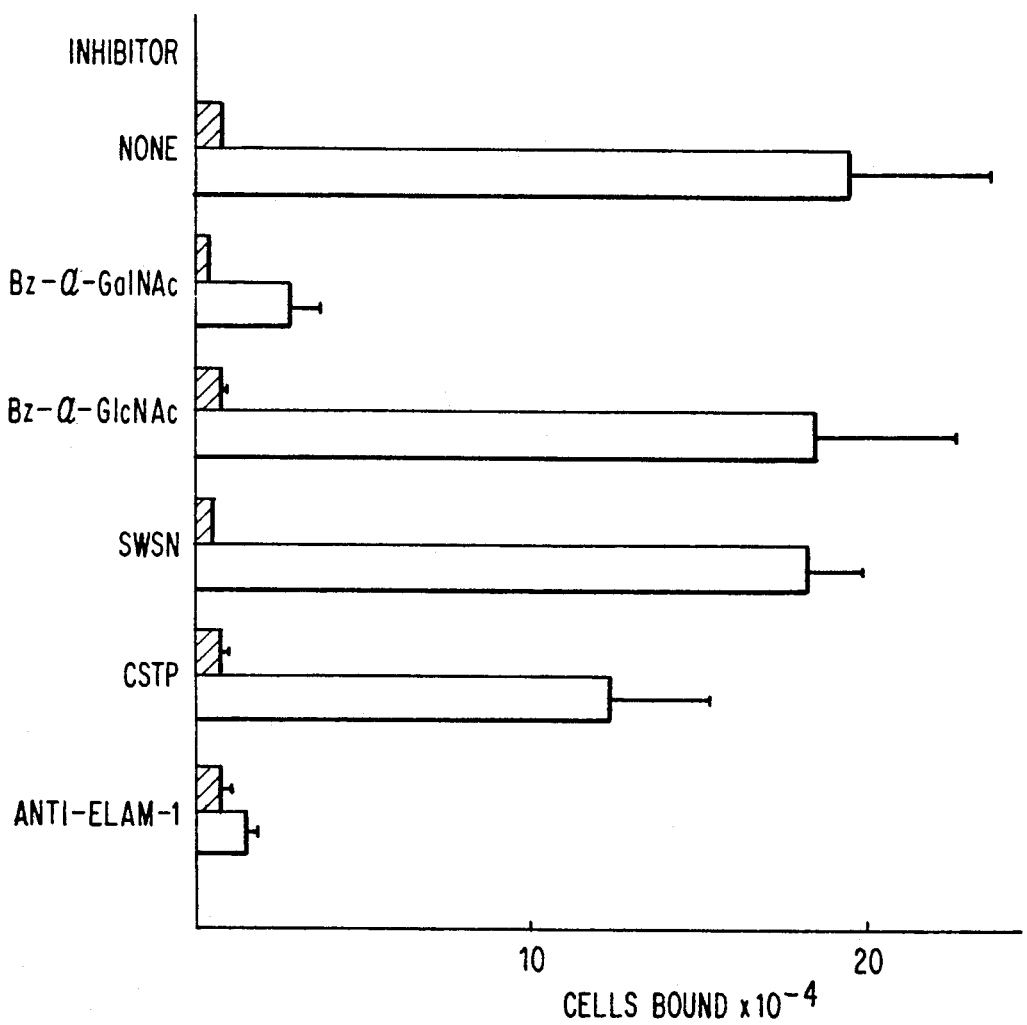
FIGS. 4A and 4B depict cell binding (HL60 in FIG. 4A; Colo205 in FIG. 4B) to unactivated (solid bars) and activated (open bars) endothelial cells. Anti-ELAM-1 is an antibody directed to a ELAM-1. DMNM indicates dimethyl-nojirimycin. SWSN swainsonine. CSTP is castanospermine. Bz-α-GlcNAc is benzyl-α-N-acetylglucosamine. TM is tunicamycin. HL60 cells were cultured with the various glycosylation inhibitors, labelled with tritium and then added to endothelial cell monolayers. Tunicamycin was toxic to HL60 cells.

Culturing of cells in the presence of various N-glycosylation inhibitors (100 μg/ml castanospermine, 10 μg/ml swainsonine and 100 μg/ml dimethyl-nojirimycin) did not inhibit the expression of SLe$^x$ or SLe$^a$ in HL60 or Colo205 cells, nor affect adhesion of those cells to HUVEC's (FIG. 4A). Although castanospermine actually increased SLe$^x$ expression in HL60 cells (FIG. 1B), the inhibitor slightly decreased adhesion of HL60 cells to HUVEC's (FIG. 4A).

Figure 4B:
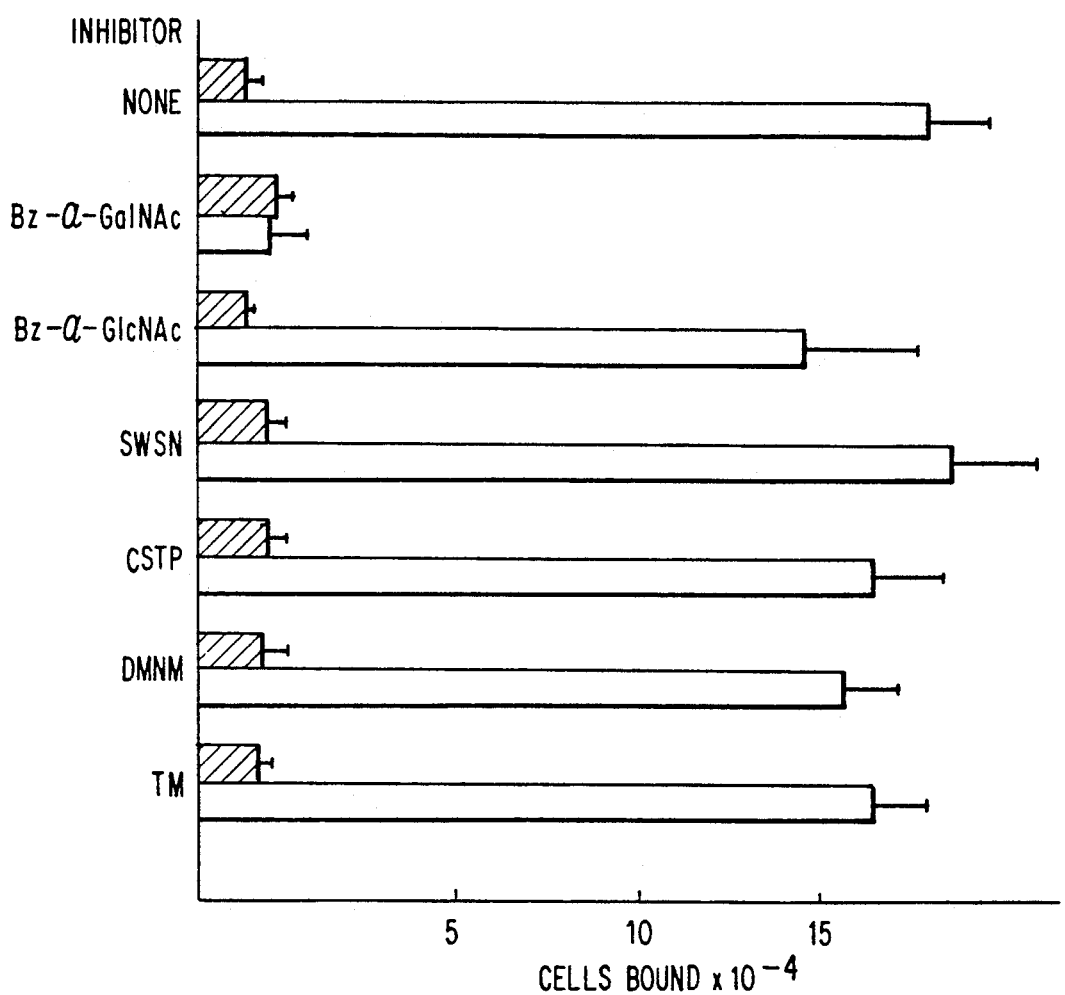

Adhesion of SLe$^x$ expressing Colo205 cells to activated HUVEC's also was not affected by the various N-glycosylation inhibitors, including 0.5 μg/ml tunicamycin (FIG. 4B). Adhesion of both HL60 and Colo205 cells on activated HUVEC's was inhibited by 2 mM Bz-α-GalNAc and not by the isomer Bz-α-GlcNAc, also used at a 2 mM concentration (FIGS. 4A and 4B). Exposure to an ELAM antibody (J. Imm., 145: 819, 1990) at a concentration of 5 μg/ml inhibited binding. The results suggest that the SLe$^x$ epitope present on N-glycosylated side chains is not recognized appropriately by selectin.

The effect of Bz-α-GalNAc on adhesion of HL60 and U937 cells to platelets activated by thrombin or by phorbol 12-myristate 13-acetate (PMA) was determined. Platelets were isolated from "platelet-rich plasma" (Oregon Red Cross, Portland, OR). Contaminating erythrocytes were removed by centrifugation (80xg for 10 minutes). Platelets were obtained by centrifugation (300xg for 10 minutes), washed once in Tyrode's buffer (pH 6.5) containing 22 mM trisodium citrate and 0.35% BSA and resuspended in the same buffer at a concentration of 1×10$^9$ platelets/ml. All procedures were performed at room temperature.

The platelet suspension (1×10$^8$/ml) in Tyrode's buffer at pH 7.2, was supplemented with thrombin (final concentration 1 U/ml) or PMA (final concentration 10$^{-7}$ M) and the mixture was incubated at 37° C. for 10 minutes without stirring. Each well of a 48-well plate (Costar Scientific, Cambridge MA) was filled with poly-L-lysine solution (100 μg/ml) in PBS and incubated for 1 hour. Each well then was washed with PBS, blocked with BSA and supplemented with 150 μl PBS containing 6×10$^7$ platelets. Plates were centrifuged (300xg for 7 minutes) and further incubated 30 minutes at room temperature.

Bound platelets were fixed by addition of 0.1% glutaraldehyde in PBS for 2 minutes at 4° C. Each well was washed with 10 mM glycine in PBS and plates were incubated with 5% BSA containing 0.1% sodium azide, 10 mM glycine in PBS for 1 hour at room temperature. After washing with culture 23 medium (RPMI 1640 containing 5% FCS), 1×10$^6$ HL60 cells or U937 cells labelled with [$^3$H]thymidine were added to each well.

After incubation for 45 minutes at room temperature, unbound cells were aspirated and wells were washed once with medium (RPMI 1640 containing 5% FCS). Bound cells were detached with 0.05% trypsin-0.02% EDTA (Irvine Scientific) in PBS and counted in a liquid scintillation counter.

Figure 5B:
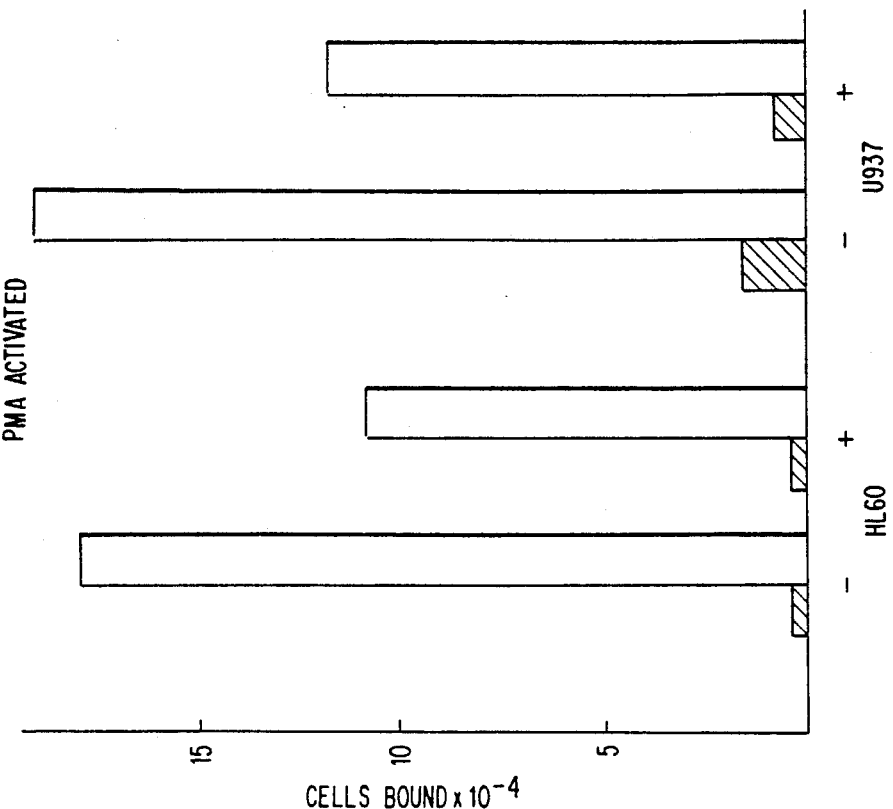
FIGS. 5A and 5B depict the binding of untreated (-) and Bz-α-GalNAc-treated (+) HL60 and U937 cells with unactivated (solid bars) or activated (open bars) platelets (activated with 18 bin in FIG. 5A and activated with $10^{-7}$ M (final concentration) phorbol 12-myristate β-acetate (PMA) in FIG. 5B).
Figure 5A:
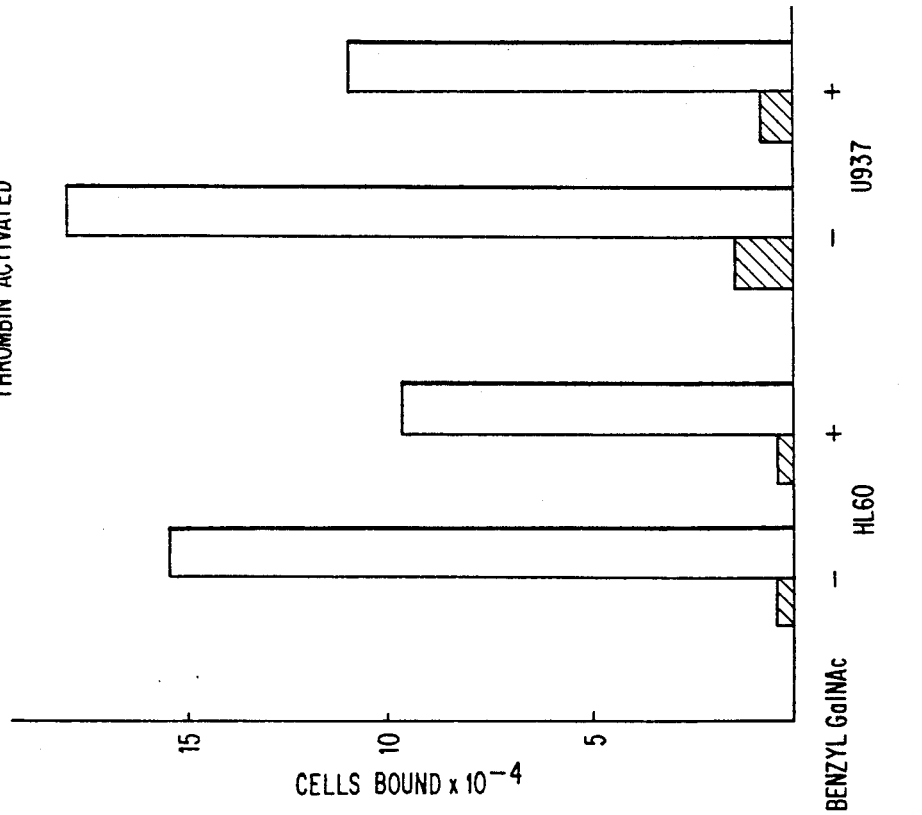

Adhesion of both HL60 and U937 cells on activated platelets was reduced significantly when cells were pretreated with Bz-α-GalNAc. The effect was observed with both thrombin-activated (FIG. 5A) and PMA-activated platelets (FIG. 5B).

While the invention has been exemplified in detail by reference to specific embodiments and examples, it will be clear to the artisan that various changes and modifications can be made therein without departing from the spirit and scope thereof.

We claim:

1. A therapeutic composition comprising a selectin-dependent adhesion inhibiting amount of an O-glycosylation inhibitor or O-glycosylation extension inhibitor, or pharmaceutically acceptable salts thereof, and a pharmaceutically acceptable diluent, carrier or excipient, wherein said inhibitor or said extension inhibitor blocks addition to a serine or threonine residue of a protein of a compound selected from the group consisting of galactose, N-acetylgalactosamine, N-acetylglucosamine, sialic acid and fucose.

2. The composition of claim 1, wherein said inhibitor is benzyle-α-N-acetylgalactosamine.

3. The composition of claim 1, wherein said inhibitor is contained within a microcapsule.

4. The composition of claim 3, wherein said microcapsule has attached onto the external surface thereof a ligand capable of binding specifically to $Le^x$, sialyl $Le^x$ or sialyl $Le^a$.

5. The composition of claim 4, wherein said ligand is $Le^x$.

6. The composition of claim 4, wherein said ligand is an antibody.

7. A method of inhibiting cell interactions comprising exposing a first cell that expresses a ligand that is specifically bound by selectin expressed on a second cell to a selectin-dependent adhesion inhibiting amount of an O-glycosylation inhibitor or O-glycosylation extension inhibitor, wherein said inhibitor or said extension inhibitor blocks addition to a serine or threonine residue of a protein of a compound selected from the group consisting of galactose, sialic acid, fucose, N-acetylgalactosamine and N-acetylglucosamine.

8. The method of claim 7, wherein said inhibitor reduces expression of sialyl-$Le^x$, sialyl-$Le^a$ or $Le^x$.

9. The method of claim 7, wherein said inhibitor is benzyl-α-N-acetylgalactosamine.

10. The method of claim 7, wherein said second cell is an endothelial cell or a platelet.

11. The method of claim 7, wherein said first cell is a leukocyte or a tumor cell.

12. The method of claim 7, wherein said inhibitor is contained within a microcapsule.

13. The method of claim 12, wherein said microcapsule has attached onto the external surface thereof a ligand capable of binding specifically to $Le^x$, sialyl $Le^x$ or sialyl $Le^a$.

14. The method of claim 13, wherein said ligand is $Le^x$.

15. The method of claim 13, wherein said ligand is an antibody.

* * * * *